United States Patent [19]

Crittenden

[11] Patent Number: 5,104,376
[45] Date of Patent: Apr. 14, 1992

[54] TORSIONALLY RIGID BALLOON DILATATION PROBE

[75] Inventor: James F. Crittenden, Hollis, N.H.

[73] Assignee: C. R. Bard, Inc., Murray Hill, N.J.

[21] Appl. No.: 458,906

[22] Filed: Dec. 29, 1989

Related U.S. Application Data

[60] Continuation of Ser. No. 303,908, Jan. 30, 1989, Pat. No. 4,917,088, which is a division of Ser. No. 729,541, May 2, 1985, Pat. No. 5,102,390.

[51] Int. Cl.$^5$ .................................................. A61M 29/00
[52] U.S. Cl. ....................................... 604/96; 606/194
[58] Field of Search ................................ 604/95–104; 606/108, 192, 194

[56] References Cited

U.S. PATENT DOCUMENTS

| | | |
|---|---|---|
| 4,195,637 | 4/1980 | Grüntzig et al. . |
| 4,292,974 | 10/1981 | Fogarty et al. ............ 128/344 |
| 4,307,722 | 12/1981 | Evans . |
| 4,323,071 | 4/1982 | Simpson et al. ............ 604/99 X |
| 4,346,698 | 8/1982 | Hanson et al. ............ 604/103 X |
| 4,362,150 | 12/1982 | Lombardi et al. ............ 600/18 |
| 4,444,188 | 4/1984 | Bazell et al. . |
| 4,456,000 | 6/1984 | Schjeldahl et al. ............ 604/49 X |
| 4,561,439 | 12/1985 | Bishop et al. . |
| 4,582,181 | 4/1986 | Samson . |
| 4,715,378 | 12/1987 | Pope, Jr. et al. ............ 606/194 |
| 4,723,936 | 2/1988 | Buchbinder et al. . |
| 4,838,268 | 6/1989 | Keith et al. . |
| 4,943,278 | 7/1990 | Euteneuer et al. ............ 604/96 |
| 4,998,917 | 3/1991 | Gaiser et al. ............ 604/96 |

FOREIGN PATENT DOCUMENTS

| | | |
|---|---|---|
| 0078311 | 5/1981 | European Pat. Off. . |
| 512456 | 9/1939 | United Kingdom ............ 128/344 |

Primary Examiner—C. Fred Rosenbaum
Assistant Examiner—C. Maglione
Attorney, Agent, or Firm—Wolf, Greenfield & Sacks

[57] ABSTRACT

Probe-like catheter has a small diameter and can be steered to and passed through narrow stenoses. The probe has a balloon at its distal end which is collapsible to a low profile to enable it to be passed through the stenosis. The probe may include a distal tip which can hold a preset curve. The probe is sufficiently rigid to enable the transmission of torque to the distal end to permit steering of the probe by controllably rotating the proximal end of the probe.

In use, a stenosis which cannot be crossed by a more conventional sized dilatation catheter may permit passage of the dilatation probe.

19 Claims, 2 Drawing Sheets

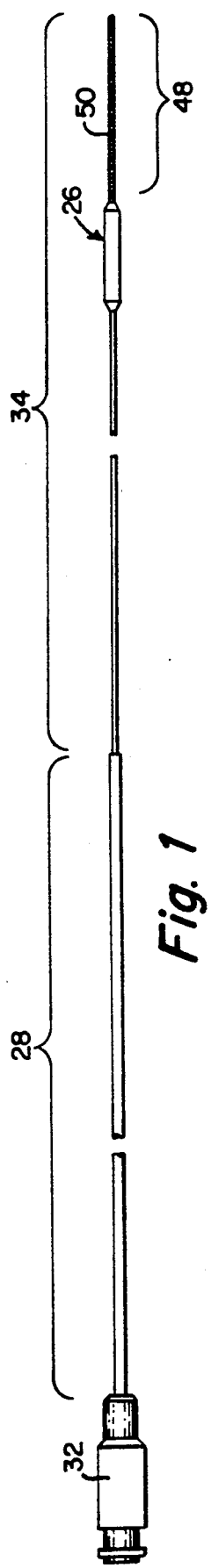
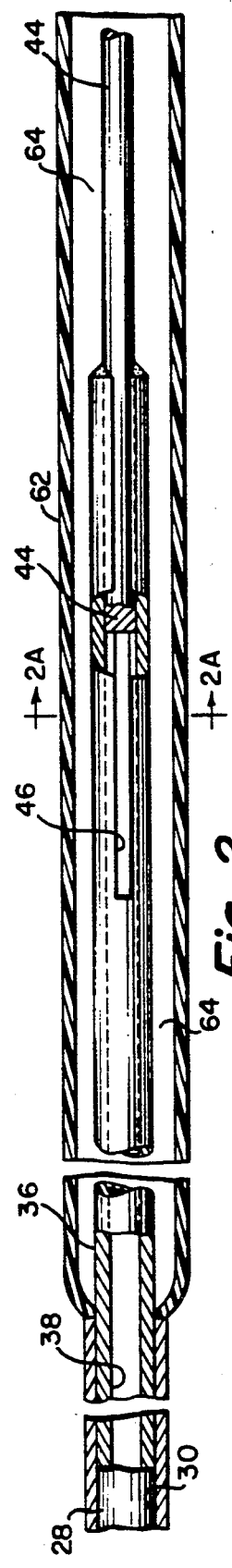
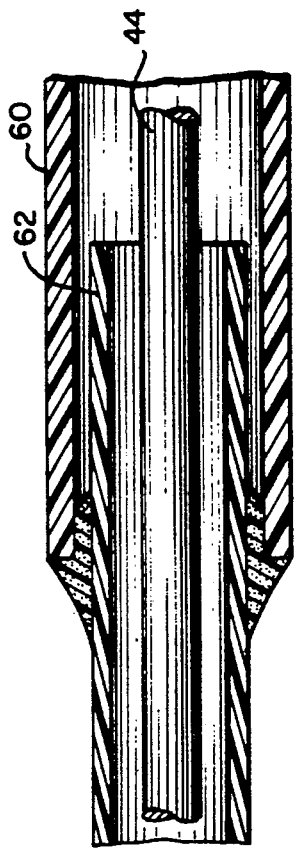
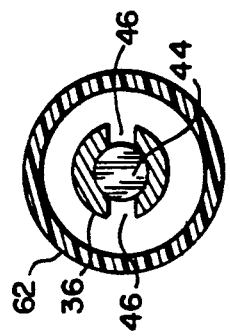
Fig. 1
Fig. 2
Fig. 2A
Fig. 4

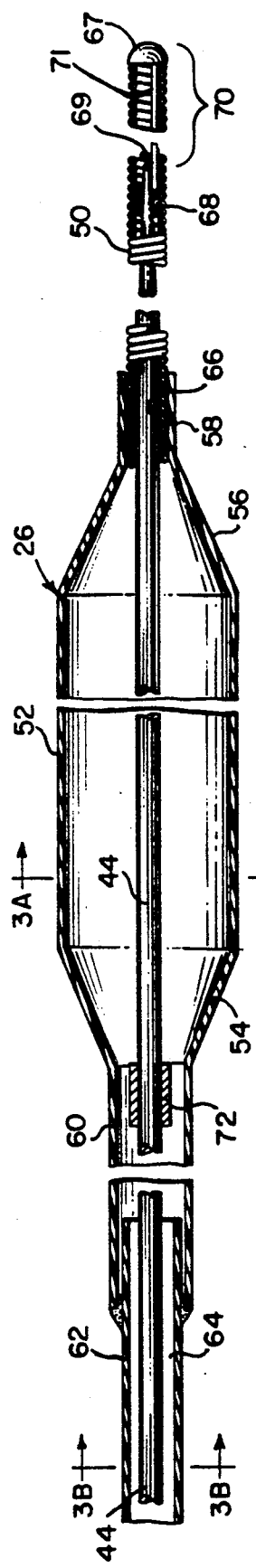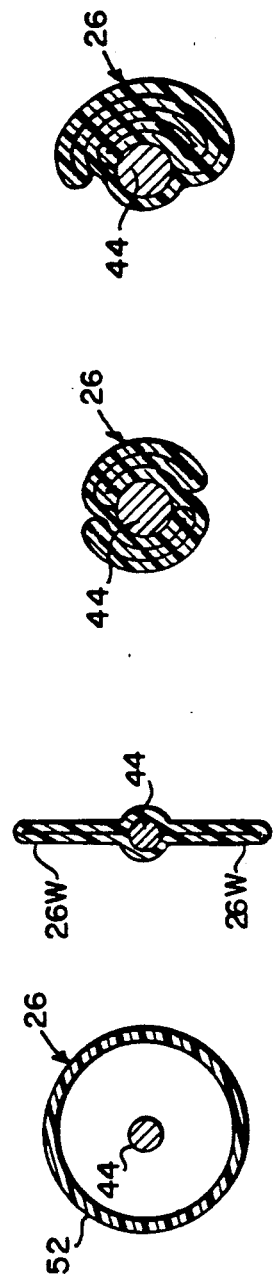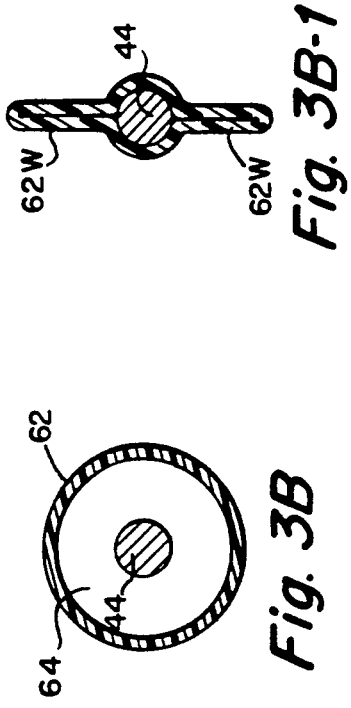

TORSIONALLY RIGID BALLOON DILATATION PROBE

RELATED APPLICATION

This application is a continuation of application Ser. No. 303,908, filed Jan. 30, 1989, now U.S. Pat. No. 4,917,088, which is a divisional of our application Ser. No. 729,541, filed May 2, 1985 now U.S. Pat. No. 5,102,390.

FIELD OF THE INVENTION

This invention relates to a new and improved catheter for performing balloon angioplasty procedures on stenosed blood vessels.

BACKGROUND OF THE INVENTION

Balloon angioplasty procedures have been used in recent years with increasing success in the treatment of obstructed arteries, such as the coronary arteries. The procedure involves advancing a catheter having a special balloon at its distal end to the location of the stenosis. The balloon portion of the catheter is placed, in its deflated condition, in the stenosis and then is inflated under high pressure to compress radially and outwardly the biological material such as plaque which forms the stenosis. Balloon dilatation systems of this type are illustrated in U.S. Pat. Nos. 4,195,637 and 4,323,071. In those situations in which balloon angioplasty can be used, its successful use avoids the greater risk of complex and expensive bypass surgery.

Not all arterial stenoses are treatable by balloon angioplasty. Among the types of vascular obstructions which have not been treatable with the angioplasty technology are those in which the passage through the stenosis is so narrow that the balloon angioplasty catheter cannot be inserted into the stenosis, even when the balloon is in its collapsed, deflated condition. Thus, where the opening in a stenosis was only enough to permit passage of a guide wire, but not enough to permit passage of a deflated angioplasty balloon, the procedure could not be performed. Until the present invention, such conditions disqualified the patient from receiving the potential benefits of the angioplasty technique. Instead, such conditions required bypass surgery.

Also among the difficulties encountered in the angioplasty technique has been the advancement and placement of the dilatation balloon catheter in the intended branch of the arterial tree so that it can be advanced into the stenosis to be treated. Difficulties often are encountered in guiding the catheter to the obstructed branch or portion of the arterial tree.

It is among the primary objects of the invention to provide a catheter which enables such very narrow stenoses to be treated with the balloon angioplasty technique, and in a manner in which the catheter can be guided accurately.

SUMMARY OF THE INVENTION

The invention involves use of a novel probe. The probe is very small in diameter and has a small diameter, thin-wall balloon at its distal portion. The probe is constructed and arranged to be advanceable through the patient's vascular system and can be controlled and manipulated from its proximal end so that it can be steered selectively at forks in the vascular system.

The main body of the probe has a flexible, elongate, hollow main shaft adapted to transmit torque without whipping. A smaller diameter balloon support wire is attached to and extends from the distal end of the flexible hollow shaft. A helical spring is mounted to the distal portion of the support wire. The probe balloon is attached at its proximal end to the distal portion of the main shaft. An inflation/deflation port is formed in the hollow main shaft, distally of the proximal balloon connection, to communicate with the interior of the balloon for inflating and deflating the balloon. The distal end of the balloon is attached to the proximal end of the helical spring. A distal segment of the probe which projects beyond the balloon, includes the helical spring and portion of the support wire. The support wire is tapered within the helical spring to provide progressively increasing flexibility in a distal direction. The distal end of the probe is adapted to be bent to a curve and enables the probe to be selectively directed and steered by rotating the probe from its proximal end.

The balloon is very thin. The diameter of the collapsed, folded balloon portion of the probe is very small and defines a very low profile.

It is among the objects of the invention to provide a balloon dilatation catheter by which an angioplasty procedure can be performed on a stenosed blood vessel in which the lumen through the stenosis is too small to permit entry of a full size angioplasty catheter.

Another object of the invention is to provide an angioplasty system which can be used to dilatate a stenosis in which the opening is as small as about 0.020 inches wide.

Another object of the invention is to provide a probe having an outer diameter approximately the same as the diameter of a guide wire.

A further object of the invention is to provide a catheter of the type described which allows the angioplasty procedure to be performed in cases which, before the invention, could not have been performed and would have required bypass surgery.

Still another object of the invention is to provide a dilatation catheter which can be manipulated from the proximal end and can be steered with control adequate to be selectively guided through a patient's arterial tree to a precise intended location.

DESCRIPTION OF THE DRAWINGS

The foregoing and other objects and advantages of the invention will be appreciated more fully from the following further description thereof, with reference to the accompanying drawings wherein:

FIG. 1 is a longitudinal, fragmented illustration of the dilatation probe;

FIG. 2 is an enlarged longitudinal section of the portion of the dilatation probe which includes the transition region from the proximal segment to the distal segment;

FIG. 2A is a sectional illustration of the transition tube as seen along the line 2A—2A of FIG. 2;

FIG. 3 is an enlarged longitudinal sectional illustration of the balloon portion and distal segment of the dilatation probe;

FIG. 3A is a sectional illustration of the probe balloon as seen along the lines 3A—3A of FIG. 3;

FIG. 3A-1 is an illustration of the probe balloon of FIG. 3A in an evacuated, collapsed configuration;

FIGS. 3A-2 and 3A-3 are illustrations of the collapsed dilatation probe balloon with its wings wrapped about the support wire in an S-shaped configuration and a C-shaped configuration, respectively;

FIG. 3B is a sectional illustration of the sleeve extension of the probe when the probe is in an inflated condition;

FIG. 3B-1 is an illustration of the sleeve of FIG. 3B when in an evacuated, collapsed configuration; and FIG. 4 is an enlarged sectional illustration of the juncture of the balloon and the balloon extension sleeve.

DESCRIPTION OF THE PREFERRED EMBODIMENT

Among the difficulties which may arise in an angioplasty procedure is that the balloon dilatation catheter which has been advanced to the location of the arterial stenosis is too large, even with the balloon deflated, to be inserted into the stenosis. The present invention provides a slender probe-like catheter having a low profile with its balloon collapsed which is adapted to be steered to and inserted into such a narrow stenosis.

As shown in FIG. 1 the dilatation probe 12 is of very slender construction having a cross-section approximately equal to that of a small diameter guide wire.

The dilatation probe 12 has a balloon 26 which, when collapsed, defines a small cross-sectional configuration so that it can pass through tight stenoses. In its collapsed configuration the probe balloon 26 as well as the remaining portions of the probe 12 define an outer diameter corresponding to that of a small diameter guide wire. As will be described in further detail, when a conventional full size dilatation catheter cannot be advanced into the lumen of the stenosis, the probe 12 can be directed to and passed within the stenosis. The probe balloon 26 then is inflated to effect the dilatation.

The probe 12, illustrated in FIG. 1, is of the order of about 180 centimeters when used in coronary arteries with a percutaneous femoral artery approach.

The probe 12 has a relatively long proximal segment 28 which is formed from narrow, solid wall tubing, such as hypodermic tubing. In the illustrative embodiment, the proximal segment 28 may be of the order of 150 centimeters long. The proximal segment 28 is rigid torsionally so that it can transmit substantially fully to its distal end rotational motion imparted to the proximal end. As will be described, the distal tip of the probe can be bent to a preset curve. Rotation applied to the probe can be controlled to selectively direct and steer the curved distal end of the probe as it is advanced. The proximal segment 28 also is flexible and can bend longitudinally to follow the curvature of the patient's arterial system. Preferably the proximal segment 28 of the probe 12 is sufficiently flexible that it can bend to follow the curve of a patient's aortic arch which has a radius of the order of between 2.5 to 3.5 inches in an adult.

As shown more clearly in enlarged FIG. 2, in the preferred embodiment of the invention the hollow tubular segment 28 has an outer diameter of 0.018 inches, a wall thickness of about 0.002 inches and an internal diameter passage 30 of 0.014 inches. A conventional fitting 32 is secured to the proximal end of segment 28 to facilitate connection with an inflation/deflation device, such as a syringe (not shown).

The probe 12 includes a distal segment 34 which extends from the distal end of the proximal segment 28 to the distal end of the probe 12. The distal segment 34 includes a narrow diameter elongate support wire 44 which is connected to and extends distally of the proximal segment 28. The support wire 44 is connected to the proximal tubing 28 by a short transition tube 36. The transition tube 36 is about one half inch long and also is formed from slender, flexible hypodermic tubing with a smaller diameter than the proximal tube 28. In the illustrative embodiment, the transition tube 36 is formed from hypodermic tubing having an outer diameter of 0.014 inches, a wall thickness of 0.003 inches and an inner diameter of 0.008 inches. The proximal end of the tubing 36 is received within the distal end of the internal passage 30 of the proximal segment 28 and is secured thereto as by soldering or brazing. The solid support wire 44 is attached to the distal end of the transition tube 36. The wire 44, which in the illustrative embodiment is very slender, preferably 0.008 inches diameter, is received in the distal end of the passage 38 of the tubing 36 and is secured by soldering or brazing. The support wire 44 plugs the distal end of the tubing 36. In order to permit the balloon 26 to be inflated and deflated, the transition tube 36 is provided with apertures 46 on opposite sides of the tube wall to provide communication with the internal passages 38, 30 of the probe. The apertures 46 may be defined by forming a pair of longitudinal slots in the wall of the tubing 36. The support wire 44 provides support for the probe balloon 26 and also extends distally beyond the balloon 26, to form the core of a leader segment 48. The leader segment includes a helically wound radiopaque coil spring 50 which is attached to the distal end of the core wire 44 in a manner described below.

The probe balloon 26 is formed by molding high strength polymeric material in a manner which provides a thin balloon wall not greater than about 0.001 inches thickness and, preferably, having a thickness of the order of 0.0005 inches. The balloon may be manufactured as described in U.S. Pat. No. 4,490,421 issued Dec. 25, 1984 and reference is made thereto for further details concerning the manufacture of the balloon.

As shown in enlarged detail in FIG. 3, the balloon includes a main cylindrical portion 52. In the illustrative embodiment, the probe balloon 26 preferably has an outer diameter of 1.3 millimeters. As mentioned above, the balloon is formed from a high strength material which will not tend to stretch when inflated. The length of the balloon 26 may be of the order of 15 millimeters. The balloon is formed to include tapering portions 54, 56 at the proximal and distal ends respectively. The distal tapering portion 56 merges into a narrowed neck 58 which fits snugly about and against the proximal end of the coil spring 50. The distal neck 58 of the probe balloon 26 is adhesively attached to the coil spring 50. As will be described in further detail, the proximal end of the coil spring is soldered securely to the core wire at the region where the distal neck 58 of the probe balloon 26 is joined. The proximal tapering portion 54 merges into a narrowed proximal neck 60.

In order to communicate the interior of the probe balloon 26 with the inflation/deflation passages 30, 38 of the tubing, an extension sleeve 62 is adhesively attached to the proximal neck 60. The extension sleeve 62 extends proximally over the support wire 44. The proximal end of the extension sleeve 62 preferably is formed from the same material as the balloon 26 and is securely and adhesively attached to the outer surface of the transition tube 36, where it joins the main tube 28. The extension sleeve 62 defines an annular passage 64 about the support wire 44. The annular passage 64 provides communication between the apertures 46 and the interior of the balloon 26 for inflation and deflation of the balloon.

As shown in FIG. 3 the leader segment 48 which extends distally of the balloon 26 is of increasing flexibility in a distal direction to provide a relatively soft, flexible leading tip which reduces the chance of trauma or injury to the blood vessel. In the illustrative embodiment the leader segment is about 3 centimeters long. The coil spring 50 is soldered, at its proximal end to the support wire 44, as indicated at 66. The distal end of the support wire 44 also is soldered to the coil spring 50 as indicated at 68. Soldered joint 68 and the distal tip 69 of the support wire 44 terminate short of the distal tip of the coil spring 50. The distal tip 70 of the coil spring 50 may extend about five millimeters beyond the soldered joint 68 and defines a highly flexible bumper tip. A rounded weld bead 67 is formed at the distal tip of the spring 50. The leader segment 48 is of increasing flexibility in a distal direction. The support wire 44 is taper ground and, for example, may be ground smoothly to a 002 inch diameter at its distal tip 69.

The distal tip 70 of the coil spring 50 includes a flexible and bendable stainless steel shaping ribbon 71 which is secured to the distal tip 69 of the support wire at one end, and to the distal weld bead 67 at its other end. The shaping ribbon is of slender, rectangular cross section, of the order of 0.001 inches by 0.002 inches. The shaping ribbon is adapted to be bent to a desired curve and to retain that curve when relaxed. The preset curve enables the probe 12 to be steered by rotation of the probe from its proximal end. The probe can be rotated to direct the prebent distal tip 70 in selective directions as desired within the patient's blood vessels.

The probe also is provided with a radiopaque marker band 72 which preferably is formed from platinum. The marker band 72 is located proximally of the main portion of the balloon 26. In the illustrative embodiment it is securely attached to the support wire 44. The marker band 72 provides a means by which the physician can verify, fluoroscopically, the position of the probe balloon 26.

In order that the probe may be passed through the lumen of a catheter which may guide the probe to the coronary arteries, the probe balloon 26 also must be collapsible to a shape and size which can be passed through the lumen of that guiding catheter. The invention accomplishes these objectives by using the slender, small diameter support wire 44 extending through the balloon and by using a balloon with a very thin but high strength wall. When the probe 12 is to be inserted through the guiding catheter, the balloon 26 first is collapsed by applying suction, such as by a syringe, to the fitting 32. The balloon 26 and the extension sleeve 62 collapse, tending to form radially projecting wings as illustrated in FIGS. 3A-1 and 3B-1, respectively. The wings 62W and 26W wrap about the support wire 44 when the probe is advanced through the main lumen of the guiding catheter. The wings 26W may wrap about the core wire 44 either in an S-shaped configuration suggested in FIG. 3A-2 or in a C-shaped configuration shown in FIG. 3A 3. In either configuration the overall diameter through the collapsed and folded balloon portion of the probe 12 includes six layers of the balloon material in addition to the diameter of the support wire 44. In accordance with the present invention, the balloon is formed from a high strength thin material having a wall thickness preferably not more than about 0.001". Thus, the aggregate diameter of six balloon layers plus the support wire is about 0.014 inches. The probe balloon thus is collapsible to a diameter which is about one fourth of its inflated diameter and which can pass easily through the main lumen of the guiding catheter.

In use a larger diameter guiding catheter through which the dilatation probe 12 can be passed is inserted initially in the patient's arterial system, usually through the femoral artery and is advanced through the aortic arch to locate the distal tip of the guiding catheter at the coronary ostium leading to the coronary artery or into the coronary artery to be treated. After the larger guiding catheter has been positioned the probe 12 is advanced through the larger catheter with its balloon 26 in a collapsed configuration illustrated in either of FIGS. 3A-2 or 3A-3. The diameter of the probe 12 is about the same as a conventional guide wire. The dilatation probe 12 thus can be advanced out of the distal opening of the guiding catheter and the balloon 26, in its collapsed configuration, can be inserted into and through the stenosis. The dilatation probe balloon 26 then may be inflated under pressure to expand forcefully the probe balloon 26 to its maximum diameter thereby enlarging the passageway through the stenosis.

A marker band 72 on the probe provides a means by which its position in the artery can be verified fluoroscopically.

When the probe balloon 26 has been inflated to enlarge the opening through the stenosis the probe balloon 26 is collapsed by aspirating the probe. The probe then may be withdrawn from the patient.

As described above, one of the features of the probe 12 is the increased flexibility of the distal segment 34 of the probe. The proximal segment 28, as described, is sufficiently flexible so that it can bend relatively easily through the aortic arch. The bend from the aorta, into the coronary ostium and thereafter through the coronary arteries are sharper and shorter radiused. The length of the more flexible distal segment 34 is sufficient so that the probe balloon can reach deeply into the arterial tree without requiring the stiffer proximal tubing 28 to pass through relatively sharp bends, such as the bend from the guide catheter to the coronary ostium. The distal segment 34, which consists substantially of the thin, flexible support wire 44 is able to make the relatively sharp bends with ease. Thus, the only portion of the probe 12 which actually enters the coronary artery is that which includes the slender support wire 44. This support wire is very flexible and is more easily bent to be able to negotiate shorter radius bends encountered in the coronary arterial tree.

The probe is highly steerable due in large measure to the solid wall of the tubing in the elongate proximal segment 28 of the probe. The tubing is substantially torsionally rigid and tends to transmit substantially all of its rotation applied at the proximal end to the distal end. Although the intermediate segment of the probe, which includes the slender 0.008 inch diameter wire is too small a diameter to effectively transmit torque over relatively long distances, the distal segment 34 is relatively short, preferably about twenty-five centimeters and, therefore, does not have too great of an adverse effect on the torque transmission from the proximal end of the probe to the distal end. The distal segment preferably is no longer than about 25 centimeters, as compared to the solid wall tubular proximal segment which is approximately 150 centimeters long. Thus, by forming a bend in the distal tip 70 of the leading segment, the direction of the probe 12 can be controlled by rotating the probe from the proximal end.

From the foregoing it will be appreciated that the invention provides a system and method by which the angioplasty technique for treating arterial stenoses can be extended to certain stenoses which previously required coronary artery bypass surgery. Moreover, the invention provides a probe which can be steered to selectively pass through the branches of a patient's arterial tree.

It should be understood, however, that the foregoing description of the invention is intended merely to be illustrative thereof and that other modifications and embodiments of the invention will be apparent to those skilled in the art without departing from its spirit.

Having thus described the invention what I desire to claim and secure by Letters Patents is:

1. A balloon coronary angioplasty probe comprising:
   an elongate tubular proximal segment having a proximal end and a distal end;
   an elongate distal segment non-rotatably attached to the proximal segment and extending distally beyond the distal end of the proximal segment the distal segment being shorter and more flexible longitudinally than the proximal segment;
   a balloon mounted on the probe about the distal segment;
   the tubular proximal segment defining a lumen for communicating the proximal end of the probe with the interior of the balloon to enable inflation and deflation of the balloon, said lumen comprising the sole lumen of the probe, the lumen terminating at the balloon;
   the tubular proximal segment and said distal segment being sufficiently torsionally rigid and the distal segment being sufficiently longitudinally flexible so that when the probe is in a configuration corresponding to that of a human aortic arch and with the distal segment in a coronary artery, the probe is capable of transmitting controllably from its proximal to its distal end rotation applied at the proximal end.

2. A probe as defined in claim 1 further comprising:
   said balloon being adapted to be deflated to a cross sectional configuration of a pair of double thickness wings, said wings being foldable into an S-shape configuration or a C-shape configuration;
   the aggregate diameter of the distal segment of the probe including six times the wall thickness of the balloon being not greater than the diameter of the proximal segment of the probe.

3. A probe as defined in claim 2 wherein the balloon is inflatable to a diameter of approximately four times the diameter of the distal segment in the region of the balloon when the balloon is collapsed and folded.

4. A probe as defined in claim 1 further comprising said distal segment being approximately 25 centimeters long;
   the proximal segment of the probe being sufficiently flexible to bend smoothly through the human aortic arch;
   the distal segment being bendable through sharper radius bends than that of the human aortic arch.

5. A probe as defined in claim 1 further comprising:
   the distal segment comprising a support wire having a smaller diameter than the outer diameter of the distal end of the proximal segment;
   the balloon being supported on the support wire with the support wire extending through the balloon; and
   means for communicating the lumen of the proximal tubular segment with the interior of the balloon.

6. A probe as defined in claim 5 wherein the means communicating the lumen of the tubular proximal segment with the interior of the balloon comprises:
   the tubular proximal segment having a wall and an outlet port formed in the distal portion of the wall, said outlet port being in communication with the interior of the balloon.

7. A probe as defined in claim 5 further comprising:
   a fitting attached to the proximal end of the proximal tube.

8. A probe as defined in claim 6 further comprising a fitting at the proximal end of the proximal tube.

9. A probe as defined in claim 5 further comprising:
   the distal end of the balloon being attached to the distal segment of the probe; and
   the proximal end of the balloon being attached to the proximal segment.

10. A probe as defined in claim 5 further comprising:
    the distal segment having a flexible leader segment which extends distally of the balloon.

11. A probe as defined in claim 10 further comprising:
    said leader segment having a tip constructed and arranged as to be bent to a preset curve to facilitate steering of the probe in response to rotation applied at the proximal end of the probe;
    the distal segment being not substantially greater than 25 centimeters in length;
    the proximal segment being of a length substantially greater than the distal segment.

12. A probe as defined in claim 10 wherein the leader segment includes the distal portion of the support wire, said leader segment further comprising a coil spring wound about the tapered distal portion of the support wire.

13. A probe as defined in claim 12 wherein the distal end of the balloon is adhesively attached to the proximal end of the coil spring.

14. A probe as defined in claim 1 further comprising:
    the distal segment having a flexible segment which extends distally of the balloon.

15. A probe as defined in claim 14 further comprising:
    said leader segment having a tip constructed and arranged as to be bent to a preset curve to facilitate steering of the probe in response to rotation applied at the proximal end of the probe.

16. A probe as defined in claim 14 wherein the leader segment includes a longitudinally flexible coil spring.

17. A balloon coronary angioplasty probe as defined in claim 1 further comprising:
    the distal segment being attached to the distal end of the proximal segment.

18. A small diameter, low profile balloon coronary angioplasty probe comprising:
    an elongate wire-like shaft including an elongate tubular proximal wire-like segment having a proximal end and a distal end, the elongate tubular proximal segment comprising metallic tubing;
    the shaft further including an elongate distal segment extending distally beyond the distal end of the proximal segment, the distal segment being shorter and more flexible longitudinally, than the proximal segment;
    a balloon mounted on the probe about the distal segment; and
    the tubular proximal segment defining a lumen for communicating the proximal end of the probe with the interior of the balloon to enable inflation and deflation of the balloon;

the tubular proximal segment of the shaft and the distal segment of the shaft being sufficiently torsionally rigid, and the distal segment being longitudinally flexible, so that when the probe is in a configuration corresponding to that of a human aortic arch and with the distal segment in a coronary artery, the probe is capable of transmitting controllably from its proximal end to its distal end rotation applied at the proximal end.

19. A probe as defined in claim 18 wherein said metallic tubing comprises hypodermic tubing.

* * * * *